US010143370B2

United States Patent
Ren et al.

(10) Patent No.: US 10,143,370 B2
(45) Date of Patent: Dec. 4, 2018

(54) OPHTHALMIC IMAGING SYSTEM WITH AUTOMATIC RETINAL FEATURE DETECTION

(71) Applicant: Novartis AG, Basel (CH)

(72) Inventors: Hugang Ren, Lake Forest, CA (US); Lingfeng Yu, Lake Forest, CA (US)

(73) Assignee: Novartis AG, Basel (CH)

( * ) Notice: Subject to any disclaimer, the term of this patent is extended or adjusted under 35 U.S.C. 154(b) by 147 days.

(21) Appl. No.: 14/309,618

(22) Filed: Jun. 19, 2014

(65) Prior Publication Data

US 2015/0366450 A1    Dec. 24, 2015

(51) Int. Cl.
| | | |
|---|---|---|
| A61B 3/10 | (2006.01) | |
| A61B 3/14 | (2006.01) | |
| A61B 3/00 | (2006.01) | |
| A61B 3/12 | (2006.01) | |
| G06T 7/00 | (2017.01) | |

(52) U.S. Cl.
CPC ............ *A61B 3/102* (2013.01); *A61B 3/0025* (2013.01); *A61B 3/12* (2013.01); *G06T 7/0012* (2013.01); *G06T 2207/10101* (2013.01); *G06T 2207/30041* (2013.01)

(58) Field of Classification Search
CPC .......... G06K 9/00; G09G 5/377; A61B 3/102; A61B 3/12; A61B 3/14
USPC ....................................................... 382/131
See application file for complete search history.

(56) References Cited

U.S. PATENT DOCUMENTS

| | | | |
|---|---|---|---|
| 2007/0287932 A1 | 12/2007 | Huang et al. | |
| 2009/0244485 A1* | 10/2009 | Walsh .................... | A61B 3/102 351/221 |
| 2010/0220914 A1* | 9/2010 | Iwase ................... | A61B 5/0066 382/131 |
| 2011/0106102 A1* | 5/2011 | Balicki ................ | A61B 3/1005 606/130 |
| 2011/0182517 A1* | 7/2011 | Farsiu .................. | A61B 5/0066 382/190 |
| 2011/0234978 A1* | 9/2011 | Hammer ................ | A61B 3/102 351/208 |

(Continued)

OTHER PUBLICATIONS

International Search Report and Written Opinion issued for PCT/US2015/031070, dated Aug. 18, 2015, 9 pgs.
(Continued)

*Primary Examiner* — Bumsuk Won
*Assistant Examiner* — Ephrem Mebrahtu

(57) ABSTRACT

A method of automatically detecting a retinal feature using an ophthalmic imaging system can include: acquiring an optical coherence tomography (OCT) image of a retina; segmenting the OCT image; generating a metric based on the segmented OCT image; detecting the retinal feature based on the metric; and providing an indication of the detected retinal feature to a user. An ophthalmic imaging system can include: an OCT system configured to acquire an image of a retina; a computing device coupled to the OCT system and configured to segment the image, generate a metric based on the segmented image, and detect a retinal feature based on the metric; and an audio/visual/tactile device in communication with the computing device and configured to provide at least one of an audio, visual, and tactile indication of the detected retinal feature to a user.

16 Claims, 7 Drawing Sheets

(56) References Cited

U.S. PATENT DOCUMENTS

| | | | | |
|---|---|---|---|---|
| 2011/0299031 | A1* | 12/2011 | Keane | G02C 7/022 351/159.75 |
| 2012/0045101 | A1* | 2/2012 | Everett | G06T 19/00 382/106 |
| 2012/0150029 | A1* | 6/2012 | Debuc | A61B 3/102 600/425 |
| 2013/0181976 | A1 | 7/2013 | Dastmalchi et al. | |
| 2014/0029820 | A1* | 1/2014 | Srivastava | A61B 3/102 382/131 |
| 2014/0055791 | A1* | 2/2014 | Iwase | A61B 3/102 356/479 |
| 2015/0042952 | A1* | 2/2015 | Uchida | A61B 3/102 351/206 |
| 2015/0272431 | A1* | 10/2015 | Fujii | A61B 3/005 351/206 |
| 2016/0128561 | A1* | 5/2016 | Terasaki | A61B 3/102 351/221 |
| 2016/0162736 | A1* | 6/2016 | Iwase | G06K 9/00617 382/131 |
| 2016/0174830 | A1* | 6/2016 | Rubin | A61B 3/102 351/206 |

OTHER PUBLICATIONS

Chiu et al., "Automatic segmentation of seven retinal layers in SDOCT images congruent with expert manual segmentation," Optics Express, 18(18), 19413-19428, (2010).

Fabritius et al., "Automated segmentation of the macula by optical coherence tomography," Optics Express 17(18), 15659-15669, (2009).

Götzinger et al., "Retinal pigment epithelium segmentation by polarization sensitive optical coherence tomography," Optics Express, 16(21), 16410-16422, (2008).

Ho et al., "Optical coherence tomography in the detection of retinal break and management of retinal detachment in morning glory syndrome," Acta Ophthalmologica Scandinavica, 225-227, (2006).

International Search Report and Written Opinion issued for corresponding International Application No. PCT/US2015/031070, dated Aug. 18, 2015, 9 pgs.

Kawazoe et al., "Evaluation of a partial retinal surface tear by optical coherence tomography," Clinical Ophthalmology, 733-734, (2011).

Wong et al., "Dye Extrusion Technique (DE-TECH), Occult Retinal Break Detection with Subretinal Dye Extrusion During Vitrectomy for Retinal Detachment Repair," vol. 29, 492-496, (2009).

Yang et al., "Automated layer segmentation of macular OCT images using dual-scale gradient information," Opt. Express 18(20), 21293-21307, (2010).

Yazdanpanah et al., "Segmentation of Intra-Retinal Layers from Optical Coherence Tomography Images using an Active Contour Approach," IEEE Med. Imaging, 30(2):484-495, (2011).

Zawadzki et al., "Adapatation of a support vector machine algorithm for segmentation and visualization of retinal structures in volumetric optical coherence tomography data sets," J Biomed Opt, 12(4):041206, (2007).

\* cited by examiner

OPHTHALMIC IMAGING SYSTEM WITH AUTOMATIC RETINAL FEATURE DETECTION

BACKGROUND

Technical Field

Embodiments disclosed herein are related to ophthalmic imaging systems. More specifically, embodiments described herein relate to automatically detecting structural features of the retina, such as retinal breaks, using optical coherence tomography (OCT).

Related Art

Structural defects in a patient's eye can lead to vision loss. For example, a retinal break can be a full-thickness defect in the neurosensory retina. A retinal break can be associated with rhegmatogenous retinal detachment, which can induce severe loss of vision. Moreover, undetected retinal breaks are the most prevalent reason for failure in retinal detachment surgery.

Conventionally, retinal breaks have been detected through careful fundus examination by a surgeon during a surgical procedure, such as vitreo-retinal surgery. This can involve en face visualization and examination using a surgical microscope. The conventional approach can be limited in its ability to detect relatively small retinal breaks. Thus, a surgeon can continue or finish a surgical procedure without appreciating the presence and/or position of a retinal break.

Some attempts have been made to increase the visibility of retinal breaks. For example, a dye-extrusion technique can involve injection of trypan blue dye into the subretinal space. Such techniques, however, can complicate the surgical procedure and are not commonly used.

Optical coherence tomography (OCT) can be a noninvasive, high resolution cross-sectional imaging modality. Some efforts have been made to visualize the retina using OCT. However, these efforts have not involved automatic detection of retinal breaks.

Accordingly, there remains a need for improved devices, systems, and methods that improve the ability to automatically detect structural features of the retina during a surgical procedure by addressing one or more of the needs discussed above.

SUMMARY

The presented solution fills an unmet medical need with a unique solution to provide automatic detection of structural defects of the retina by using OCT images to analyze one or more retinal layers. A surgeon can be alerted upon detection of a retinal break or other feature during a surgical procedure.

Consistent with some embodiments, a method of automatically detecting a retinal feature using an ophthalmic imaging system includes: acquiring an OCT image of a retina; segmenting the OCT image; generating a metric based on the segmented OCT image; detecting the retinal feature based on the metric; and providing an indication of the detected retinal feature to a user.

Consistent with some embodiments, an ophthalmic imaging system includes: an OCT system configured to acquire an image of a retina; a computing device coupled to the OCT system and configured to segment the image, generate a metric based on the segmented image, and detect a retinal feature based on the metric; and an audio/visual/tactile device in communication with the computing device and configured to provide at least one of an audio, visual, and tactile indication of the detected retinal feature to a user.

Additional aspects, features, and advantages of the present disclosure will become apparent from the following detailed description.

Figure 1:
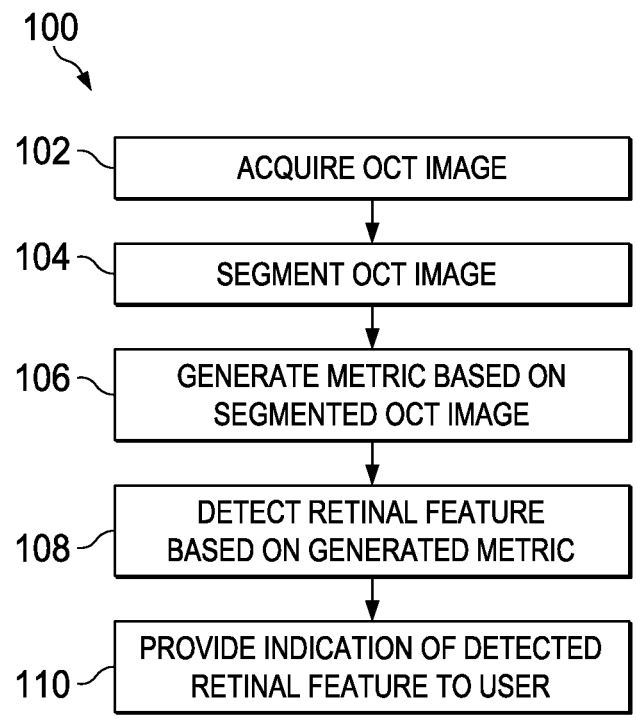
FIG. 1 is a flow diagram illustrating a method of automatically detecting a retinal feature using an ophthalmic imaging system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The present disclosure describes devices, systems, and methods for automatically detecting a retinal feature using quantitative image analysis of a retinal OCT image. One or more retinal layers, such as the inner limiting membrane (ILM) and the retinal pigment epithelium (RPE), can be identified when the OCT image is segmented. A metric or retinal layer parameter describing the geometry of one or more retinal layers (e.g., thickness of the neurosensory retina, concavity/convexity of the ILM, radius of curvature of the ILM, etc.) can be generated based on the segmented OCT image. The retinal feature can be detected using the metric or retinal layer parameter. For example, a retinal break can be detected when the thickness of the neurosensory retina is less than a threshold, when the ILM is concave in the area of the retinal feature, and/or when the radius of curvature of the ILM in the area of the retinal feature is greater than a threshold. An audio, visual, and/or tactile indication can be provided to the surgeon during the surgical procedure when the retinal feature is detected.

The devices, systems, and methods of the present disclosure provide numerous advantages, including: (1) reducing the surgeon's burden in searching for retinal defects; (2) reducing surgical procedure failures by minimizing undetected retinal defects; (3) improving surgical procedure outcomes by automatically detecting retinal defects and allowing for those defects to be addressed; and (4) increasing surgical procedure efficiency by automatically alerting the surgeon to a detected retinal defect.

FIG. 1 provides a flow diagram of a method 100 of automatically detecting a retinal feature using an ophthalmic imaging system. The method 100 can include acquiring an OCT image of a retina (step 102). The method 100 can include segmenting the OCT image (step 104). The method 100 can include generating a metric based on the segmented OCT image (step 106). The method 100 can include detecting the retinal feature based on the metric (step 108). The method 100 can include providing an indication of the detected retinal feature to a user (step 110). The steps of method 100 can be performed by one or more components of an ophthalmic imaging system (e.g., ophthalmic imaging system 600 of FIG. 6).

Method 100 can include, at step 102, acquiring an OCT image of the retina. An OCT system (e.g., OCT system 620 of FIG. 6) can acquire data associated with the OCT image. The OCT system can include an imaging probe configured to penetrate a portion of a patient's eye and image the interior of the patient's eye, including the retina. An external OCT system can be configured to image the eye, including the retina, while positioned external relative to the patient's eye. A computing device (e.g., computing device 610 of FIG. 6) can process the data acquired by the OCT system to generate the OCT image.

The OCT system can be configured to split an imaging light received from a light source into an imaging beam that is directed onto target biological tissue (e.g., by the imaging probe) and a reference beam that can be directed onto a reference mirror. The OCT system can be a Fourier domain (e.g., spectral domain, swept-source, etc.) or a time domain system. The OCT system can be further configured to receive the imaging light reflected from the target biological tissue (e.g., captured by the imaging probe, the external OCT system, etc.). The interference pattern between the reflected imaging light and the reference beam is utilized to generate images of the target biological tissue. Accordingly, the OCT system can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

Figure 2A:
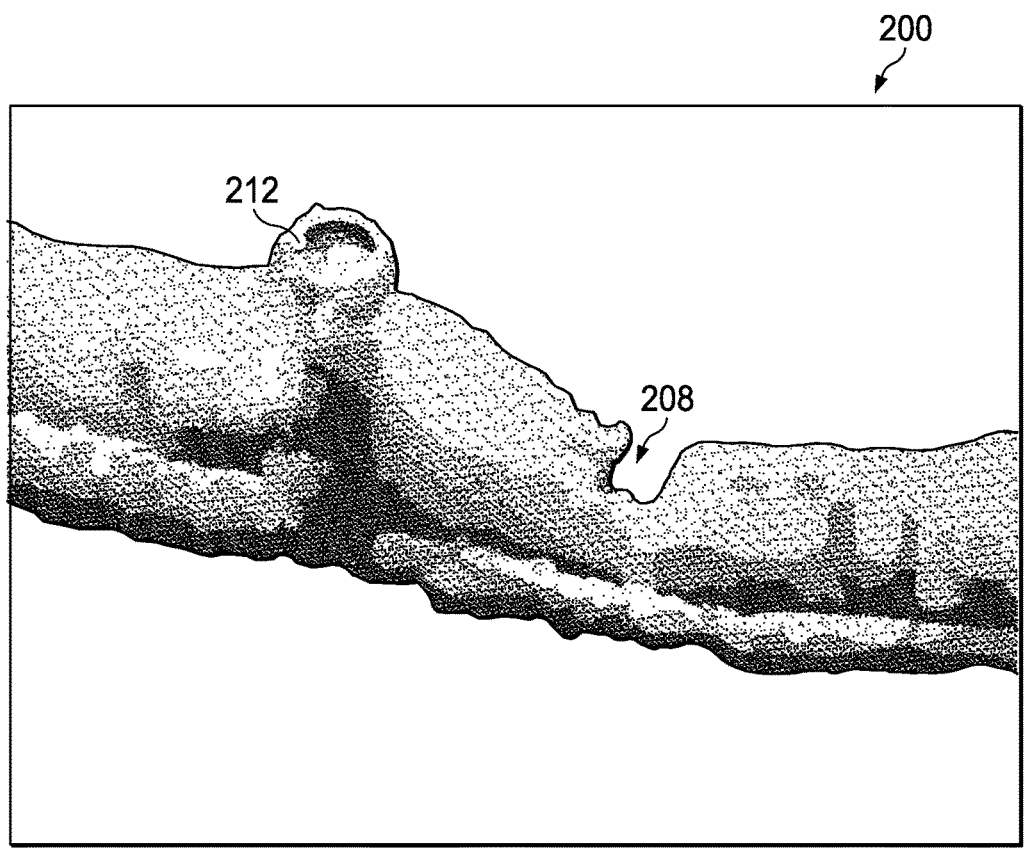
FIG. 2a is a two-dimensional OCT image of a retina.
Figure 2B:
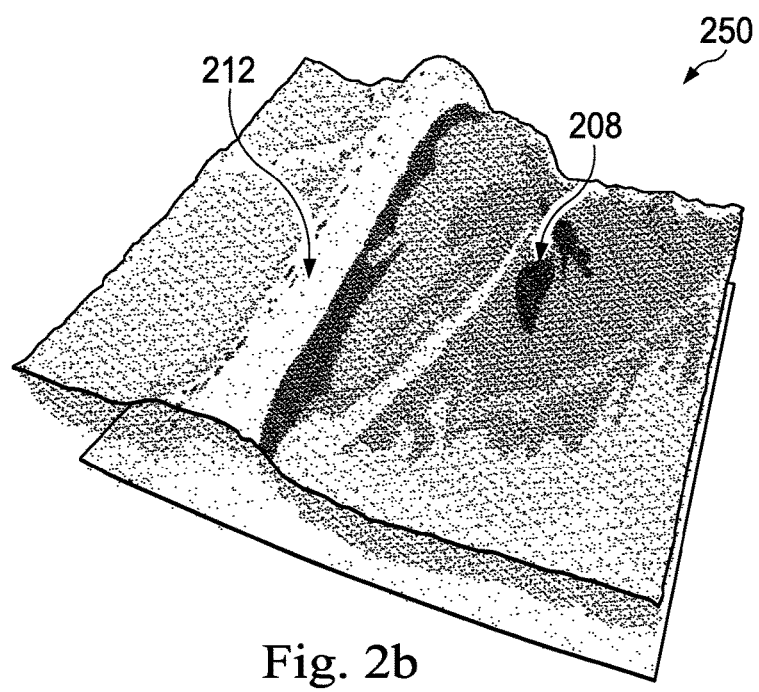
FIG. 2b is a three-dimensional OCT image of a retina.

The OCT image can be two-dimensional or three-dimensional. For example, FIG. 2a provides a two-dimensional OCT image 200 of a portion of the retina, and FIG. 2b provides a three-dimensional OCT image 250 of a portion of the retina. A retinal break 208 can be seen on the right side of FIGS. 2a and 2b. The retinal break 208 can be automatically detected using the systems, methods, and devices described herein. A blood vessel 212 can be seen on the left side of FIGS. 2a and 2b.

Figure 3A:
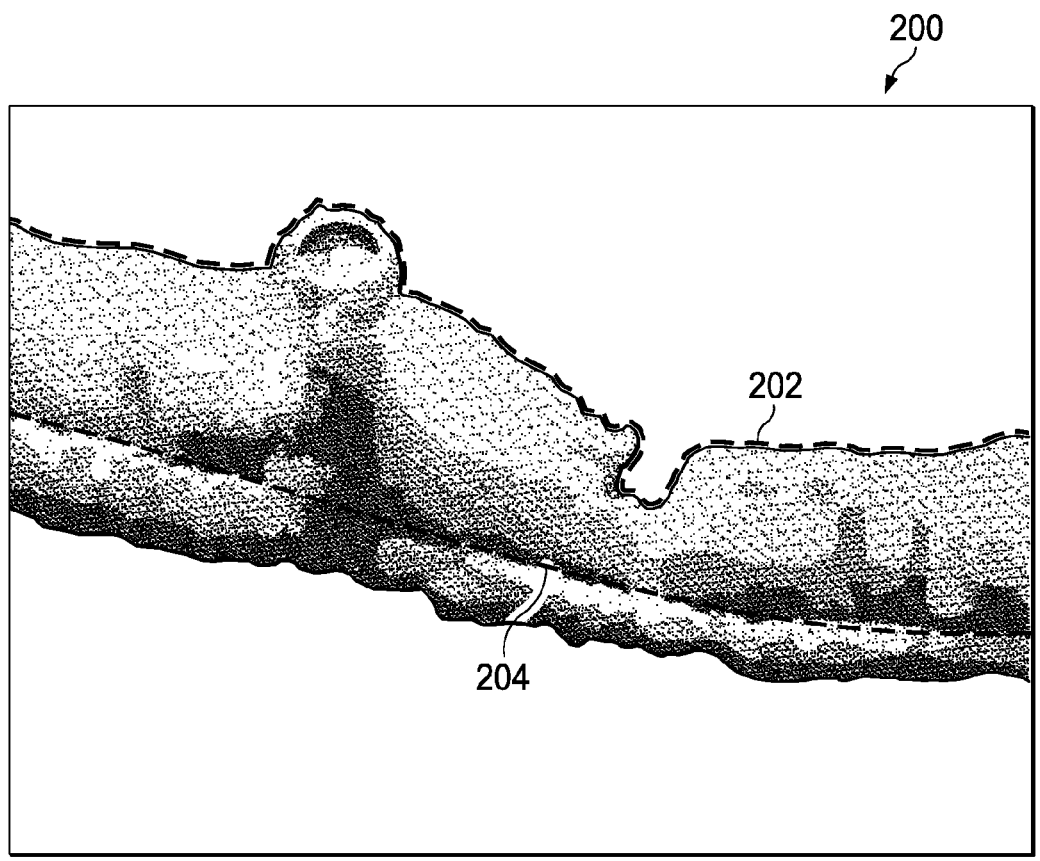
FIG. 3a is a two-dimensional OCT image of a retina.
Figure 3B:
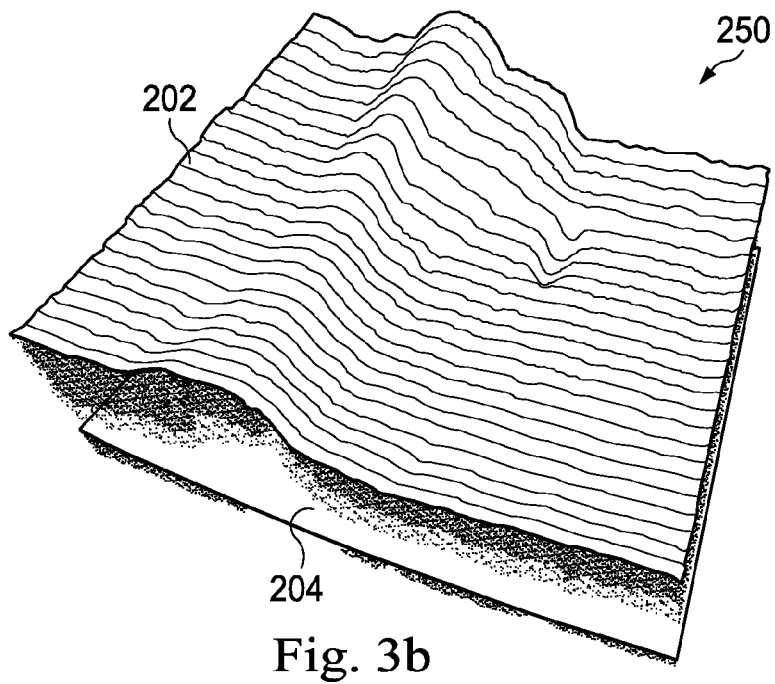
FIG. 3b is a three-dimensional OCT image of a retina.

Method 100 can include, at step 104, segmenting the OCT image. The computing device can identify one or more retinal layers using the data associated with the OCT image. Segmenting the OCT image can include identifying an inner limiting membrane (ILM), a nerve fiber layer, a ganglion cell layer, an inner plexiform layer, an inner nuclear layer, an outer plexiform layer, an outer nuclear layer, an external limiting membrane, a layer of rods and cones, a retinal pigment epithelium (RPE), and/or other retinal layer(s). FIG. 3a provides the two-dimensional OCT image 200 with boundaries of an ILM layer 202 and an RPE layer 204 identified. Similarly, FIG. 3b provides the three-dimensional OCT image 250 with boundaries of the ILM layer 202 and the RPE layer 204 identified.

Method 100 can include, at step 106, generating a metric based on the segmented OCT image. The metric can be a retinal layer parameter that objectively represents a geometry of one or more retinal layers using, for example, one or more numerical values. The retinal layer parameter can be a thickness, an intensity, a phase, a speckle size, a vascular density, a size, a concavity/convexity, and/or a radius of curvature of one or more retinal layers. For example, generating the metric can include determining a numerical representation of the concavity/convexity of the ILM. For example, a radius of curvature of the ILM in the area of the retinal feature can be determined. The retinal layer parameter can be determined using any one, two, three, four, or more retinal layers. Generating the metric can include determining a thickness of the neurosensory retina using, for example, the ILM and RPE. The thickness of the neurosensory retina can include a distance between the ILM and RPE. A numerical representation of the thickness can be used as the metric. The retinal layer parameter can be determined using one retinal layer and a strip of predefined thickness that surrounds the one retinal layer. Two or more metrics can be generated and utilized to evaluate the retina.

Method 100 can include, at step 108, detecting one or more retinal features based on the generated metric. The detected retinal feature can be a structural aspect of the retina that is indicative of a defect. For example, the retinal feature can be a break, a hole, a tear, a dialysis, a growth, a protrusion, a depression, a region with subretinal fluid, etc. Multiple retinal features and/or types of retinal features can be detected. The retinal feature(s) can be detected using one or more of the metrics. For example, the thickness of the neurosensory retina and the concavity/convexity of the ILM can be utilized. Utilizing more than one metric can advantageously increase the certainty of retinal feature detection.

Detecting the retinal feature can include comparing the retinal layer parameter to the threshold. For example, when the generated metric (step 106) includes the thickness of the neurosensory retina, detecting the retinal feature can include comparing the thickness to a threshold thickness. The retinal feature can be detected when the retinal layer parameter, such as thickness of the neurosensory retina, among others, is greater than or less than the threshold. For example, a retinal break or a retinal hole can be detected when the thickness is less than the threshold. On the other hand, a growth or a protrusion of the retina can be detected when the thickness is greater than the threshold. The threshold thickness can be in the range of, for example, 50 microns to 300 microns, 75 microns to 300 microns, 100 microns to 250 microns, or other suitable range. Thickness varies along the retina (e.g., at or near the fovea, peripheral retina, etc.), and the threshold can be selected based on a position along the retina where the retinal feature is located.

Detecting the retinal feature using the generated metric (step 106) can include analyzing whether the one or more retinal layers, such as the ILM, among others, has a concave or convex shape and/or the degree of the concavity/convexity (e.g., the radius of curvature). For example, an ILM in the area of the retinal feature that is concave can be indicative of a retinal break or a retinal hole, whereas an ILM that is convex can be indicative of a growth or a protrusion in the retina. In that regard, detecting the retinal feature can include comparing a radius of curvature of the ILM in the area of the retinal feature to a threshold radius of curvature indicative of the presence of the retinal feature. A retinal feature can be detected when the radius of curvature is greater than or less than the threshold. For example, a retinal break or a retinal hole can be detected when a concave portion of the ILM has a radius of curvature less than the threshold. The threshold radius of curvature for detecting a retinal break can be in the range of, for example, between about 0.1 mm and about 12 mm, between about 1.0 mm and about 6 mm, or between about 2.0 mm and about 4.0 mm, including values such as 10 mm, 9 mm, 8 mm, 7 mm, 6 mm, 5 mm, 4 mm, 3 mm, 2 mm, 1 mm, or other suitable value. A combination of the concavity/convexity and the corresponding radius of curvature can be utilized to detect the retinal feature.

The threshold(s) used in detecting the retinal feature can be adaptive or patient-specific. For example, a threshold can be a percentage difference in the neurosensory retina thickness compared to adjacent areas. Thus, a retinal feature can be detected when an area of the patient's neurosensory retina has a thickness greater than or less than, e.g., 50% of the thickness of adjacent areas. Similarly, a retinal feature can be detected when the radius of curvature of the ILM in the area of the retinal feature is greater than or less than, e.g., 50% of the radius of curvature of adjacent areas. The threshold can be between, for example, 1%-100%, 1%-75%, 1%-50%, 1%-25%, etc. The one or more thresholds can be selected based on empirical data. For example, a collection or database of patients can be used to determine a fixed, normal range of neurosensory retina thickness for patients with similar characteristics. Thus, a retinal feature can be detected when an area of the patient's neurosensory retina has a thickness outside of (e.g., greater than or less than) the fixed, normal range expected for the patient. Such empirical data can be used to determine a default threshold value, which may be adjusted based on patient specific characteristics. While this discussion specifically mentions thickness of the neurosensory retina, it is understood that the concavity/convexity, radius of curvature, and/or other metrics can be similarly patient-specific or more generally applicable.

Figure 4:
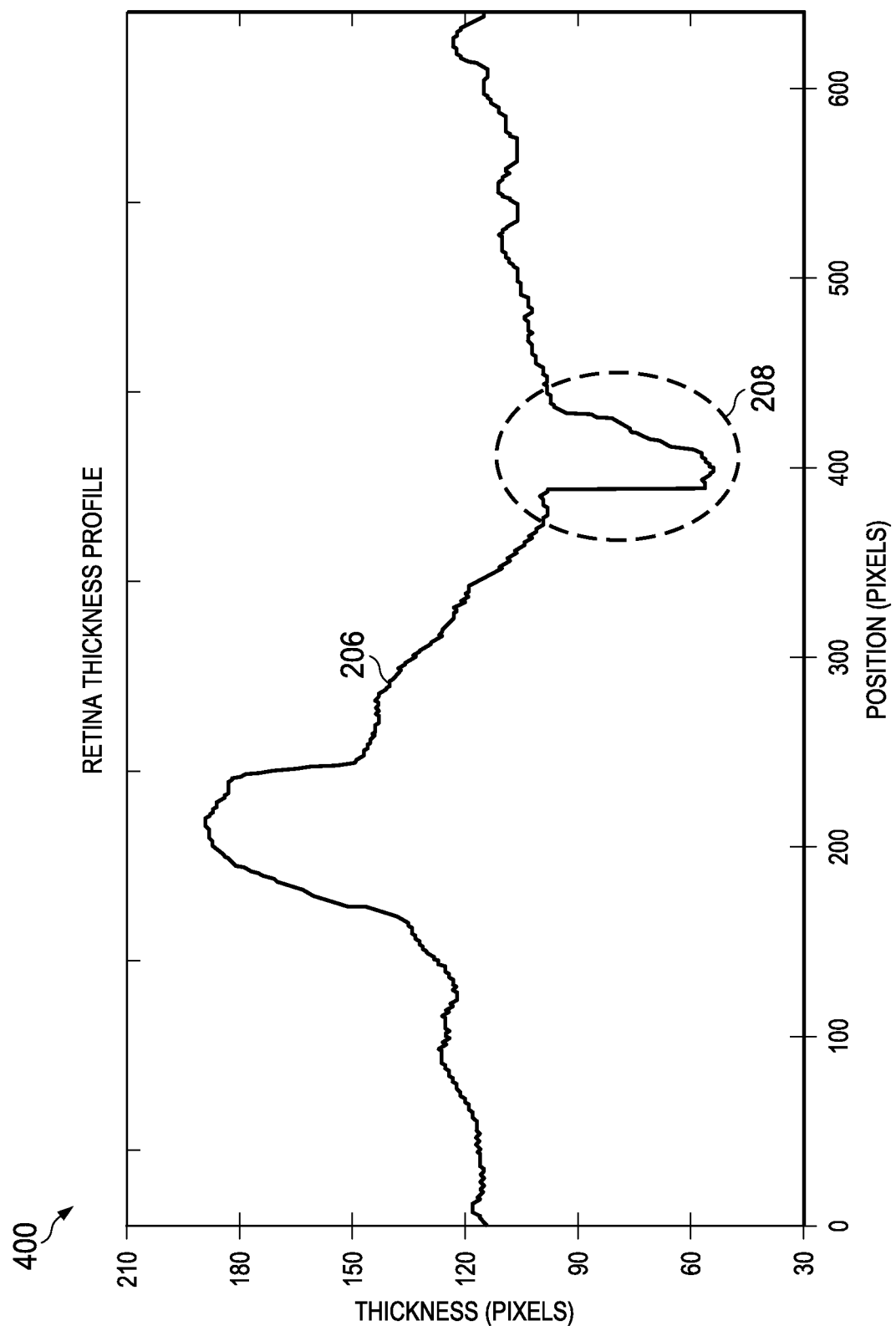
FIG. 4 is a chart illustrating a thickness profile of a retina.

FIG. 4 provides a chart 400 that is representative of a thickness profile of the neurosensory retina. The data associated with the chart 400 can be based on the segmented OCT image. The x-axis of the chart 400 can represent the position along the neurosensory retina in units of pixels. The y-axis can represent the thickness of the neurosensory retina in units of pixels. A curve 206 can represent the distance of the ILM from the RPE along the retina. The neurosensory retina thickness depicted in chart 400 can be the metric used to detect the retinal break 208. The retinal break 208 can be an area along the neurosensory retina with a thickness that is significantly different from adjacent areas (e.g., less than 50%) and/or an area with a thickness less than a fixed, normal range. While this discussion specifically mentions thickness of the neurosensory retina, it is understood that the concavity/convexity, radius of curvature, and/or other metrics can be similarly used to detect the retinal break or other retinal feature.

Figure 5A:
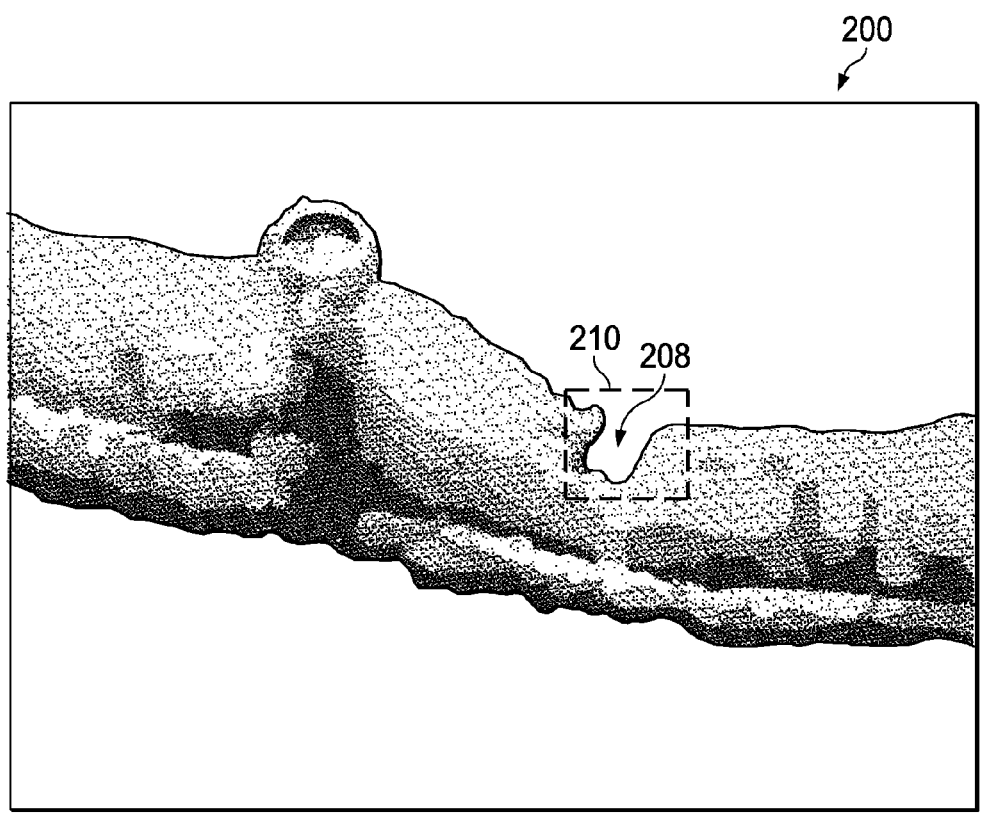
FIG. 5a is a two-dimensional OCT image of a retina.

Method 100 can include, at step 110, providing an indication of the detected retinal feature to a user. For example, an audio, visual, and/or tactile indication can be provided using an audio/visual/tactile device (e.g., audio/visual/tactile device 630 of FIG. 6). The indication can alert the surgeon, during the surgical procedure, as to the presence and/or position of the detected retinal feature. As shown in FIG. 5a, an indication 210 of the detected retinal break 208 can be a geometrical object (e.g., a square, a circle, a polygon, an ellipse, etc.) positioned around the retinal break 208. The indication 210 can be overlaid on and/or otherwise combined with the OCT image 200, and the combined OCT image can be output to the audio/visual/tactile device.

Figure 5B:
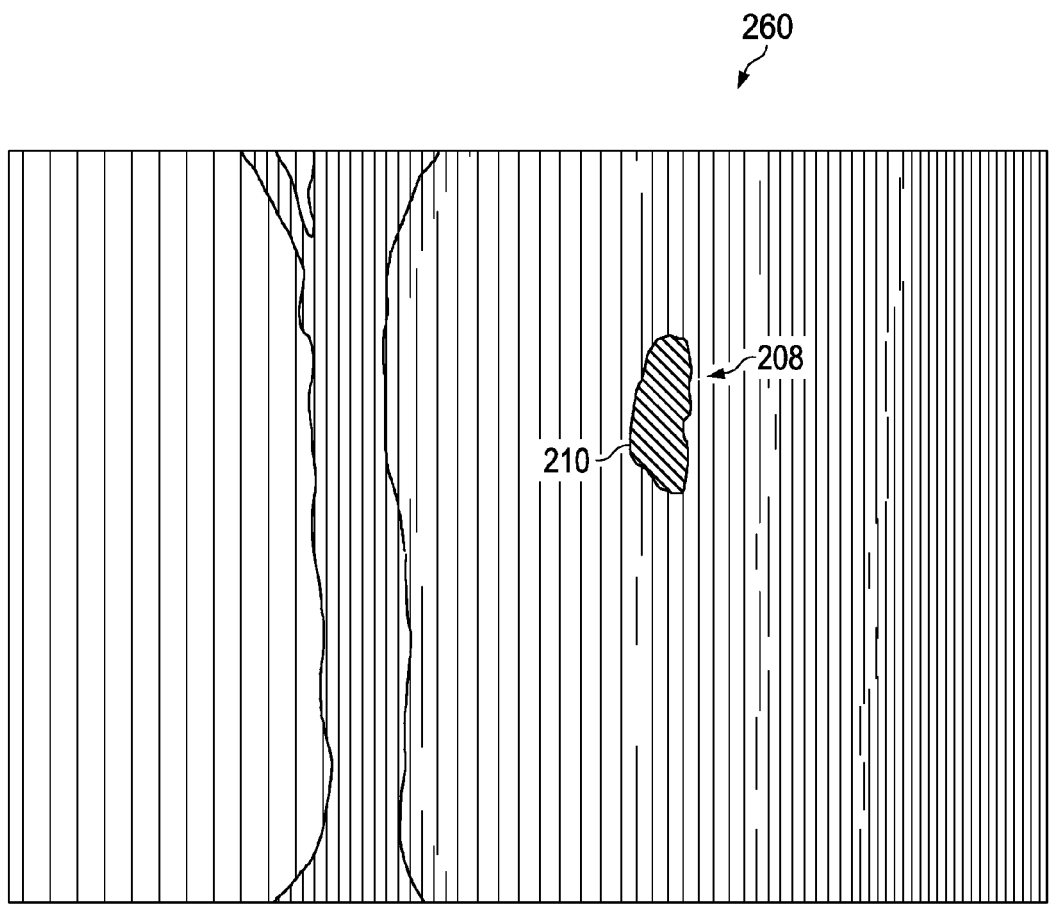
FIG. 5b is a fundus image of a retina.

As shown in FIG. 5b, the indication 210 can be shaped based on the detected retinal break 208. As also shown in FIG. 5b, the indication 210 can be overlaid on and/or otherwise combined with a fundus image 260 of the eye (e.g., instead of the two-dimensional OCT image 200) and the combined fundus image can be output to the audio/visual/tactile device.

Figure 5C:
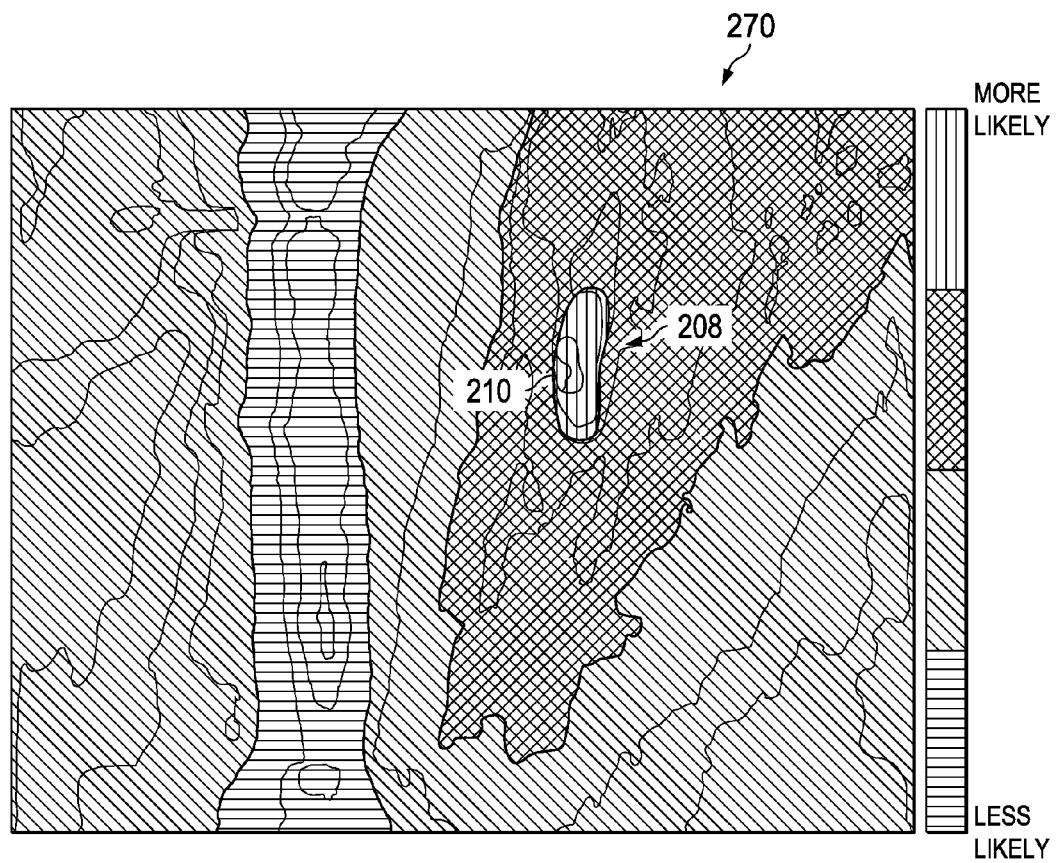
FIG. 5c is a pseudo color map representative of a likelihood of a retinal feature.

As shown in FIG. 5c, a pseudo color map 270 can be generated based on the detected retinal break 208. The pseudo color map 270 can be representative of the likelihood of the presence of a retinal feature at a given location of the retina. The indication 210 can be an area of the pseudo color map 270 that illustrates a high likelihood of the retinal feature being positioned in the area. The pseudo color map can be output to the audio/visual/tactile device.

Generally, the indication 210 can include text, one or more other shapes or symbols, and/or other visual alerts. The indication 210 can be variously positioned relative to the retinal feature. The indication 210 can include an audible signal to alert the user/surgeon to the presence and/or position of a detected retinal feature. The indication 210 can include tactile and/or haptic feedback to the surgeon.

Figure 6:
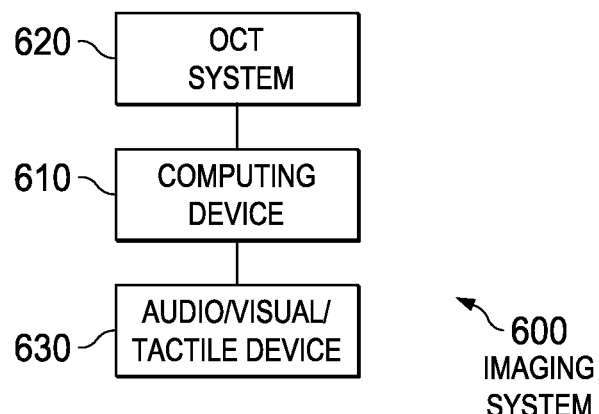
FIG. 6 is a diagram illustrating an ophthalmic imaging system.

FIG. 6 provides a block diagram of an ophthalmic imaging system 600. The imaging system 600 can include an OCT system 620 that is configured to acquire an image of the retina. The imaging system 600 can include a computing device 610 that is configured to segment the image, generate a metric based on the segmented image, and detect a retinal feature based on evaluation of the generated metric. The computing device 610 and the OCT system 620 can be configured to perform features similar to those described above. The imaging system 600 can include an audio/visual/tactile device 630 in communication with the computing device 610 and configured to provide at least one of an audio, visual, and tactile indication of the detected retinal feature. The audio/visual/tactile device 630 can be a stand-alone device and/or a component that is part of the computing device 610 or the OCT system 620. For example, the audio/visual/tactile device 630 can be a display device with integrated speakers.

Embodiments as described herein can provide devices, systems, and methods that facilitate automatic detection of structural defects in the retina by analyzing retinal OCT images. The devices, systems, and methods described herein can be used with any imaging modality in which the position, geometry, and/or contour of one or more retinal layers can be identified. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic imaging system configured to automatically detect a retinal break, comprising:
   an optical coherence tomography (OCT) system configured to acquire an OCT image of a retina;
   a non-transitory computer-readable medium storing instructions that, when executed, cause an image processor to:
   segment the OCT image;
   generate a plurality of metrics based on the segmented OCT image, wherein the plurality of metrics includes:
   a thickness of a neurosensory retina; and
   a radius of curvature of an inner limiting membrane (ILM);
   compare the thickness of the neurosensory retina and the radius of curvature of the ILM in a first area of the retina with the thickness of the neurosensory retina and the radius of curvature of the ILM in a second area of the retina which is adjacent to the first area; and based on the comparison, determine that the thickness of the neurosensory retina in the first area is less than the thickness of the neurosensory retina in the second area and the radius of curvature of the ILM in the first area is less than the radius of curvature of the ILM in the second area; and in response to the determination, generate an indicator to identify a location of the retinal break in the first area; and a display communicatively coupled to the image processor and configured to provide the indicator identifying the location of the retinal break to a user.

2. The system of claim 1, wherein the non-transitory computer-readable medium stores instructions that, when executed, cause the image processor to:

determine a difference in the thickness of the neurosensory retina in the first area of the retina and the second area of the retina meets or exceeds a threshold.

3. The system of claim 1, wherein the non-transitory computer-readable medium stores instructions that, when executed, cause the image processor to:

determine a difference in the radius of curvature in the first area of the retina and the second area of the retina meets or exceeds a threshold.

4. The system of claim 2, wherein the image processor is further configured to adjust the threshold based on patient-specific characteristics.

5. The system of claim 3, wherein the image processor is further configured to adjust the threshold based on patient-specific characteristics.

6. The system of claim 1, further comprising a tactile device coupled to the processor and configured to provide tactile or haptic feedback indicating the detected retinal break.

7. The system of claim 1, wherein the OCT system comprises at least one of:

an imaging probe configured to penetrate a portion of an eye and to image an interior of the eye; and an external OCT system configured to image the eye while positioned external relative to the eye.

8. The system of claim 1, wherein the OCT system is configured to acquire a three-dimensional OCT image.

9. The system of claim 1, wherein the non-transitory computer-readable medium stores instructions that, when executed, cause the image processor to:

generate a combined image comprising a visual indication of the retinal break overlaid on the OCT image or a fundus image; and provide the combined image to the display.

10. The system of claim 1, wherein the non-transitory computer-readable medium stores instructions that, when executed, cause the image processor to:

generate a pseudo color map representative of a likelihood of the presence of the detected retinal break; and provide the pseudo color map to the display.

11. A system, comprising:

an optical coherence tomography (OCT) imaging system configured to acquire an OCT image of a retina;

a non-transitory computer-readable medium storing instructions that, when executed, cause a processor to:

segment the OCT image;

generate a plurality of metrics based on the segmented OCT image, wherein the plurality of metrics includes:

a thickness of a first retinal feature in a first area of the retina and a second area of the retina; and a radius of curvature of a second retinal feature in the first area of the retina and the second area of the retina;

wherein the first and the second areas of the retina are adjacent;

compare the thickness of the first retinal feature and the radius of curvature of the second retinal feature in the first area with the thickness of the first retinal feature and the radius of curvature of the second retinal feature in the second area;

determine that the thickness of the first retinal feature in the first area differs from the thickness of the first retinal feature in the second area and the radius of curvature of the second retinal feature in the first area differs from the radius of curvature of the second retinal feature in the second area;

based on the determination, generate at least one of an audio, visual, and tactile indicator to indicate a location of a probable retinal break to a user.

12. The system of claim 11, further comprising:

a display; and wherein the non-transitory computer-readable medium stores instructions that, when executed, cause the processor to:

generate a combined image comprising the visual indicator overlaid on the OCT image or a fundus image; and provide the combined image to the display.

13. The system of claim 11, further comprising:

a display; and wherein the non-transitory computer-readable medium stores instructions that, when executed, cause the processor to:

generate a pseudo color map representative of a probability of the location of the retinal break; and provide the pseudo color map to the display.

14. The system of claim 11, further comprising a tactile device configured to provide tactile or haptic feedback indicating the location of at least one of the first area and the second area based on the tactile indicator generated by the instructions.

15. The system of claim 11, wherein the first retinal feature comprises a neurosensory retina and the second retinal feature comprises an inner limiting membrane (ILM).

16. The system of claim 11, wherein the OCT image comprises a three-dimensional OCT image.

* * * * *